United States Patent [19]

Camp

[11] 4,253,685
[45] Mar. 3, 1981

[54] STEAM-TIGHT JUNCTION FOR TUBULAR ELEMENTS

[76] Inventor: Nat Camp, Campillary Systems, Inc., Gettysburg, Pa. 17325

[21] Appl. No.: 43,704

[22] Filed: May 30, 1979

[51] Int. Cl.³ .............................................. F16L 53/00
[52] U.S. Cl. ........................................ 285/41; 285/24; 285/187; 285/332; 285/404; 285/423
[58] Field of Search .................. 285/41, 187, 404, 399, 285/423, 332, 24; 403/28, 29, 30; 128/200.14, 203.27

[56] References Cited

U.S. PATENT DOCUMENTS

| | | | |
|---|---|---|---|
| 3,088,758 | 5/1963 | Chilton | 403/28 X |
| 3,507,522 | 4/1970 | Froman et al. | 285/187 |
| 3,692,334 | 9/1972 | Doyle | 285/41 |
| 3,807,772 | 4/1972 | Delisle | 285/187 |

FOREIGN PATENT DOCUMENTS 1030936  5/1966  United Kingdom .................... 285/332

*Primary Examiner*—Dave W. Arola
*Attorney, Agent, or Firm*—Fidelman, Wolffe & Waldron

[57] ABSTRACT

A junction for tubular elements comprising tapered and coacting male and female elements. The male element expands more than the female element which expands under conditions of use involving exposure to steam and heat to form a steam-tight joint.

6 Claims, 3 Drawing Figures

STEAM-TIGHT JUNCTION FOR TUBULAR ELEMENTS

BACKGROUND OF THE INVENTION

This invention relates primarily to a steam-tight joint, and more specifically, to such a joint for use in a steam vaporizer.

A major problem with steam generating equipment in a vaporizier, such as disclosed in my previous U.S. Pat. Nos. 3,894,537 and 3,743,780, is the necessity for frequent cleaning to remove scale deposits. A boiling chamber consisting of a lower water chamber having electrodes immersed therein and a separate upper steam chamber may be provided. Mechanical means, such as screws and gaskets, are required to seal the junction of the upper and lower chambers to make it steam tight, while still having them readily separable for cleaning purposes. Since the boiling chamber is immersed in a water reservoir and the steam is generated by electrodes immersed in water in the lower chamber, any water leakage through a faulty seal from the boiling chamber to the water reservoir would cause the latter to become electrically charged to a dangerous degree and also cause the water in the reservoir to overheat.

SUMMARY

The present invention provides a steam-tight joint between two tubular elements, such as an upper steam chamber and a lower water chamber. The steam-tight joint comprises coacting tapered surfaces on the two elements which expand on exposure to steam or heat and thus form a tight seal. This novel construction eliminates the need for gaskets and special mechanical means for making the joint steam-tight.

It is the principal object of this invention to provide a mechanically simple, inexpensive and effective means to provide a steam-proof seal between two tubular elements.

It is a further object of this invention to provide a steam-proof seal between two tubular elements wherein the seal comprises a tapered coacting junction which expands on exposure to steam and heat to form a tight seal.

Further objects will become apparent from the description of the invention set forth.

DESCRIPTION OF PREFERRED EMBODIMENTS

Figure 1:
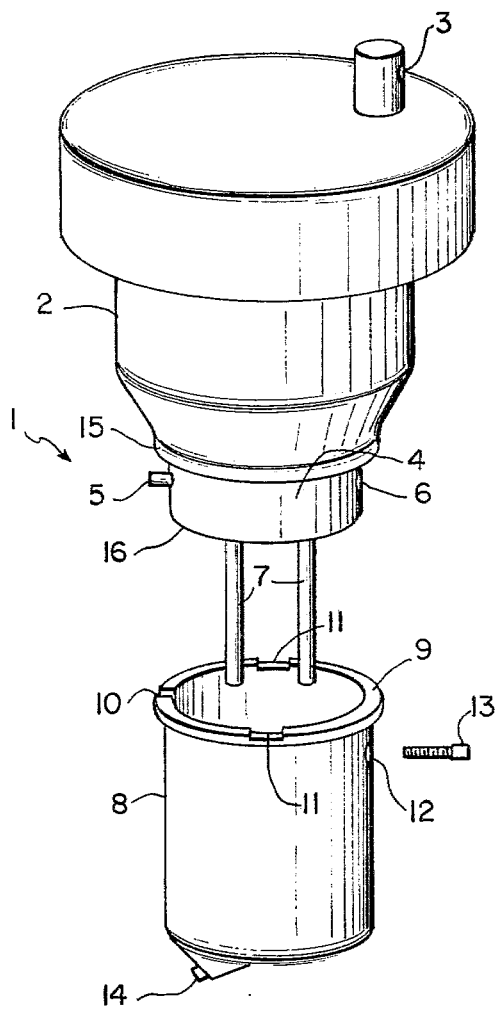
FIG. 1 is a simplified perspective drawing of the boiling chamber showing the steam chamber separated from the water chamber.

In FIG. 1, numeral 1 represents generally the boiling chamber. Reference numeral 2 is the upper steam chamber and 3 is the steam exit nipple. At the lower portion of 2 is a male junction section 4 of a smaller diameter which has a boss 5 and a threaded hole 6.

Electrodes 7, 7 centered in the upper steam chamber extend downwardly beyond section 4 into a water chamber 8. When the electrodes are immersed in water in chamber 8 and current passing therethrough by means of the electrodes, steam is generated. This is shown in detail in prior U.S. Pat. No. 3,727,265.

Chamber 8 has an upper rim 9 having a slot 10 adapted to receive boss 5 and shallow slots 11, 11. A hole 12 is located at the upper portion of 8 which is adapted to fit over hole 6 in the upper steam chamber 2 when chambers 2 and 8 are brought together. When holes 6 and 12 are in registry screw 13 is screwed through said holes to keep the upper and lower chambers from accidental separation. Water inlet 14 for introducing water into the lower chamber is located at the bottom of 8.

Figure 2:
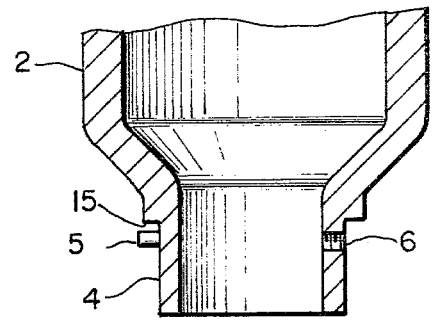
FIG. 2 is an enlarged cross section of the upper portion of the steam chamber.
Figure 3:
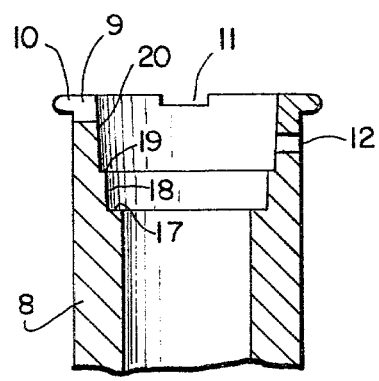
FIG. 3 is an enlarged cross section of the lower portion of the water chamber.

The structure of the junction elements of chambers 2 and 8 which form the novel seal of this invention is shown in FIGS. 2 and 3. As shown in FIG. 2, an annulus shoulder 15 is present at the lower portion of 2, and male junction section 4 extends from the inner portion of the shoulder to end. The outer surface of 4 has a inward taper. A slope of about 1° has been found to be suitable, but this may be varied by a relatively small amount without affecting the results significantly.

In FIG. 3, an annulus shoulder 17 is present at the inner surface of 8 as shown. The distance of 17 from end rim 9 is slightly more than the length of 4 from 15 to 16, whereby end 16 is slightly above shoulder 17 when chambers 2 and 8 are brought together.

Extending upwardly from shoulder 17 is a portion 18 having a length of about one fourth the distance from 17 to the top of 9. This fraction may vary somewhat without substantially affecting the operation and the sealing results of this invention. The slope of 18 is the same as that of 4 in the upper steam chamber. At the upper end of 18 is located an additional annulus shoulder 19 having a small width, such as about 0.03 inches in this embodiment. This too may vary slightly without serious effect. Extending from the outer edge of shoulder 19 to the top of 9 is a tapered section 20 having the same slope as 4 and 18. As is obvious, all the tapered sections are tapered cylindrical surfaces. The clearance between 4 and 18 is only a few thousands of an inch when the elements are cold. When hot the elements expand to form a tight seal. A larger clearance exists between 4 and 20, above shoulder 19. This serves to relieve stresses due to heat expansion and thus prevents cracking in section 20.

The operation of the junction is as follows: The male element 4 of chamber 2 is inserted into the open portion of chamber 8, so that the lower portion of 4 contacts 18 in chamber and the top portion of rim 9 contacts shoulder 15. Steam and heat generated by current flow through electrodes 7 immersed in water in 8, cause expansion of 4, and 18 as well as 20, forming the tight seal. Boss 5 and coacting slot 10 guide the upper and lower chambers 2 and 8 into proper position. Slots 11, 11 permit the chambers to be pried apart by a screwdriver blade or the like. Rim 9 and shoulder 15 provide thicker band of material to strengthen the end portions to resist any stresses occasioned by the prying action, especially when the chambers bind while they are hot.

With some materials employed to make the unit 1, such as phenolic resins, at least some of the expansion is due to water absorption at the ends units 2 and 8 during the steam generation. With other materials, e.g. metals, the expansion is due to entirely to heat alone.

While the description of the sealing means has been given with specific reference to steam generating equipment for a vaporizer, it is believed obvious that the seal design is not limited thereto. It may be employed to provide a junction for tubular elements containing or conveying hot fluids other than steam or water. The expansion of the tapered elements under the influence heat and/or the specific fluid serves to form the seal.

I claim:

1. A male and female junction for first and second tubular elements, said first tubular element having a first end, a stop means on said first tubular element spaced from the said first end, a male junction portion of reduced diameter with a length extending from the first end to said stop means and having an inward taper, the second tubular element having a second end, a female junction portion at the interior of the second element adapted to form a tight seal with said male junction portion comprising, a first annular shoulder at the interior of said second tubular element and located from the second end slightly more than the length of the male junction portion, a tapered frustro conical surface extending from said first annular shoulder toward the second end for a fraction of said length to form a step portion, a second annular shoulder having a small width at the top of the step portion, a tapered frustro conical surface extending from the second annular shoulder to the second end, all of the tapered surfaces having the same slope, a first clearance of only a few thousands of an inch separating the male and female junction portions, whereby the male junction portion is adapted to abut against the step portion of the female junction between the first and second annular shoulder portions and to form a tight seal when the elements expand on being exposed to internal heat or hot vapors, a second clearance larger than said first clearance separating the male and female junction portions in the region between the second annular shoulder and the second end whereby to relieve stresses due to heat expansion and thus prevent cracking of the second tubular element.

2. The junction of claim 1 wherein said first tubular element has a boss on the male junction portion and said second tubular element has in the tapered cylindrical surface extending from the second annular shoulder to the second end a slot adapted to receive said boss.

3. The junction of claim 2 wherein said second tubular element has at the second end an enlarged rim, the said rim having at least one shallow indentation therein.

4. The junction of claim 3 wherein the said tubular elements are integral, respectively with a steam chamber and a boiling chamber.

5. The junction of claim 3 wherein the elements comprise a phenolic resin.

6. The junction of claim 4 wherein the elements comprise a phenolic resin.

* * * * *